United States Patent [19]

Nakagawa et al.

[11] 4,082,802
[45] Apr. 4, 1978

[54] PROCESS FOR THE PREPARATION OF AROMATIC SECONDARY OR TERTIARY AMINO COMPOUNDS

[75] Inventors: Masataka Nakagawa, Yamatotakada; Tadasu Iga, Suita; Akira Fukura, Ibaragi, all of Japan

[73] Assignee: Sumitomo Chemical Company, Limited, Osaka, Japan

[21] Appl. No.: 423,702

[22] Filed: Dec. 11, 1973

Related U.S. Application Data

[63] Continuation-in-part of Ser. No. 134,071, Apr. 14, 1971, abandoned.

[30] Foreign Application Priority Data

Apr. 28, 1970  Japan .................................. 45-37013

[51] Int. Cl.$^2$ .................... C07C 91/16; C07C 87/52
[52] U.S. Cl. ................................. 260/574; 260/438.1; 260/577
[58] Field of Search ........................... 260/577, 574

[56] References Cited

U.S. PATENT DOCUMENTS

| 2,137,407 | 11/1938 | Lazier ........................ 260/580 X |
| 2,479,657 | 8/1949 | Wilkes ........................ 260/268 |
| 2,969,394 | 1/1961 | Chenicek ..................... 260/577 |
| 3,223,734 | 12/1965 | Fallstad et al. ................ 260/583 |
| 3,397,237 | 8/1968 | Jackson ....................... 260/576 |

FOREIGN PATENT DOCUMENTS

| 1,324,155 | 3/1963 | France. |
| 2,061,709 | 6/1971 | Germany ..................... 260/577 |
| 43-15601 | 7/1968 | Japan ........................ 260/577 |
| 6,814,770 | 4/1969 | Netherlands. |
| 568,230 | 3/1945 | United Kingdom ............ 260/577 |
| 172,819 | 7/1965 | U.S.S.R. ...................... 260/577 |

OTHER PUBLICATIONS

Chem. Abstract, 73:109400p (1970).
Houben-Weyl, 4th edition, vol. 11/1, pp. 126 & 343.
I.E.C. Prod. Res. Develop. 1, 179-181 (1962).
Adkins, *Organic Reactions*, vol. VIII, pp. 8-9 (1954).
Rice et al., *J.A.C.S.*, vol. 77, pp. 4052-4054 (1954).
Corson et al., *J. Org. Chem.*, vol. 21, p. 474 (1956).
Emerson, "Org. Reactions", vol. IV, p. 178 (1949).

*Primary Examiner*—Ethel G. Love
*Attorney, Agent, or Firm*—Stevens, Davis, Miller & Mosher

[57] ABSTRACT

Aromatic secondary or tertiary amino compounds of the formula,

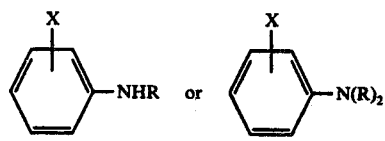

wherein X is a hydrogen atom, a methyl group or a methoxygroup, and R is a $C_1$–$C_4$ alkyl group, are produced by reacting hydrogen and an aromatic nitro compound of the formula,

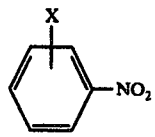

wherein X is as defined above, with an alcohol of the formula,

ROH wherein R is as defined above, in the presence of a catalyst of copper chromite.

5 Claims, No Drawings

PROCESS FOR THE PREPARATION OF AROMATIC SECONDARY OR TERTIARY AMINO COMPOUNDS

CROSS REFERENCE TO THE RELATED APPLICATION

This application is a continuation-in-part of copending application Ser. No. 134,071, filed Apr. 14, 1971, now abandoned.

The present invention relates to a process for producing aromatic secondary or tertiary amino compounds. Particularly, the invention relates to a process for producing aromatic secondary or tertiary amino compounds which comprises reacting hydrogen, an aromatic nitro compound and an aliphatic alcohol in the presence of a copper chromite catalyst.

Various processes for producing aromatic secondary or tertiary amino compounds have been heretofore known. For example, the sulfuric acid catalyst process [Unit Process in Organic Chemistry, page 850 (1958)], the concentrated phosphoric acid catalyst process (U.S. Pat. No. 2,991,311) and the alumina catalyst process [Chemisches Zentralblatt, page 2579 (1953)], each of these three processes comprising reacting aniline with an alcohol in the presence of each said catalyst, and a process which comprises reacting an aromatic nitro compound with an aldehyde in an alcohol solvent in the presence of a Raney nickel catalyst (Journal of American Chemical Society, Vol. 62, page 69, 1940) are enumerated as typical processes.

However, all of these processes are very disadvantageous from a commercial point of view in that the catalyst used is difficult to handle or the starting aldehyde or aniline is expensive.

It is, therefore, the principal object of the present invention to avoid the difficulties heretofore encountered in prior art processes.

It is a further object of the present invention to provide a process for producing aromatic secondary or tertiary amine compounds easily at a low cost.

These and other objects and advantages of the invention will appear from the following description of the invention.

As a result of various studies, the present inventors have found that these objects can be accomplished by providing a process for producing secondary or tertiary amino compounds of the formula (I) or (II).

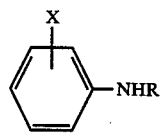
(I)

or

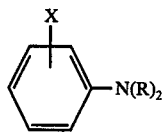
(II)

wherein X is a hydrogen atom, a methyl group or a methoxy group, and R is a $C_1$–$C_4$ alkyl group, which comprises reacting hydrogen, an aromatic nitro compound of the formula (III),

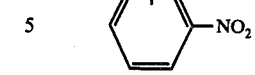
(III)

wherein X is as defined above, and an alcohol of the formula (IV),

ROH        (IV)

wherein R is as defined above, in the presence of a catalyst of copper chromite.

According to the present process, reduction and alkylation occur simultaneously as follows;

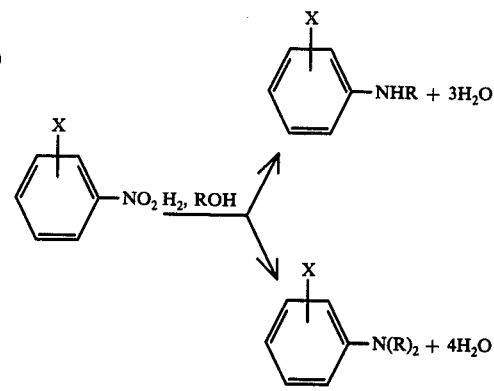

wherein R and X are as defined above.

The copper chromite catalyst used in the present invention contains copper chromite of the formula, $CuOCuCr_2O_4$, as a main ingredient, and can easily be prepared by a process as described in "Organic Reaction," Vol. 8, page 9 (1954). If necessary, a small amount of one or several elements of Fe, Ni, Ba, Mg or Mn may be added as a promotor to copper chromite. Further, a small amount of diatomaceous earth, sodium silicate, kaolin, graphite, pumice stone, and active carbon may be contained as a vehicle or a carrier. In general, these catalysts are commercially available in the form of tablet or powder. Commercially available copper chromite catalysts are, for example, JET oxide produced by I.C.I. and N 201, N 202, N 203 and N 208 copper chromite catalysts produced by NIKKI CHEMICAL CO., LTD.

Examples of the aromatic nitro compounds of the formula (III) synthesized according to a known process include nitrobenzene, 2-methylnitrobenzene, 3-methylnitrobenzene, 4-methylnitrobenzene, 2-methoxynitrobenzene, 3-methoxynitrobenzene and 4-methoxynitrobenzene.

The alcohol of the formula (IV) include methyl alchol, ethyl alcohol, n-propyl alcohol, isopropyl alcohol, n-butyl alcohol, isobutyl alcohol and sec.-butyl alcohol.

Whether the product obtained is the secondary or tertiary compound, depends upon molar ratios of the starting materials, and there is a usual tendency that the predominant reaction to produce a secondary compound proceeds with use of a smaller molar ratio of the alcohol to the nitro compounds, and to produce a tertiary compound with use of a larger molar ratio thereof.

The present reaction can be conducted according to either a pressure catalytic process or a vapor phase catalytic process. The vapor phase catalytic process is, however, preferable in that any one of the secondary compound or the tertiary compound may be produced according to demand because a mixing ratio of the aromatic nitro compound and the aliphatic alcohol can be freely changed and in that the reaction may be carried out in a continuous manner.

A molar ratio of the alcohol to the aromatic nitro compound may be of any value not less than one, but the reaction reaches equilibrium at a molar ratio of about 20 : 1. Therefore, the molar ratio is preferably 1 : 1 to 20 : 1. When the more excess amount of the alcohol is used, the unreacted alcohol may be recovered and repeatedly used.

The reaction temperature is preferably 150° to 400° C in both pressure catalytic and vapor phase catalytic processes. In the pressure catalytic process, the reaction is preferably carried out at a pressure of 20 to 100 atmospheres for 5 to 60 hours.

After the completion of the reaction, an oil layer separated is subjected to a fractional distillation to obtain the desired compound. The compounds obtained by the above procedures are enough pure for practical use. However, if necessary, it may be further purified by the recrystallization process, the rectification process, the column chromatography process or the formic acid treatment process ["Industrial and Engineering Chemistry," Vol. 28, page 33 (1936)].

The thus obtained aromatic secondary amino compounds and/or aromatic tertiary amino compounds are useful as intermediates in general chemical industry, particularly intermediates for dyestuffs, agricultural chemicals and rubber chemicals.

The following examples will serve to illustrate the practice of the present invention in more detail, but do not limit the scope of the invention.

REFERENCE EXAMPLE

PREPARATION OF COPPER CHROMITE CATALYST

Into a 3,000 ml three necked flask equipped with a stirrer, a thermometer and a funnel, was placed 1,300 ml of water, 550 g of cupric nitrate [$Cu(NO_3)_2 \cdot 3H_2O$] and 300 g of ammonium dichromate were added thereto. The mixture was stirred for 3 hours to dissolve the solids. Successively, 330 g of 2.6% aqueous ammonia solution was added gradually to the solution through the funnel to adjust pH to 7.0. The reddish yellow precipitates produced were filtered, washed with about 500 ml of water and dried at 80° to 90° C for about 20 hours. The resulting powder was placed in a calcination furnace and agitated without interruption at 340° C. The reddish yellow powder was changed to black through brown with the generation of a gas. The calcined black powder was stirred for 30 minutes in 500 ml of 10% aqueous acetic acid solution, and thereafter filtered, washed six times with 200 ml of water and dried at 120° C for 12 hours, whereby 325 g of copper chromite was obtained as black powder.

A mixture of 325 g of copper chromite powder thus obtained, 55 ml of water, 65 g of 30% aqueous sodium silicate solution and 0.1 g of graphite was kneaded for 30 minutes in a 1000 ml kneader. The resulting mixture was formulated into granules having a diameter of 0.5 mm to 1.0 mm by means of a granulator. The granules were dried at 90° C for 10 hours and thereafter formulated into cylindrical rods having a height of 0.5 mm and a diameter of 5 mm by means of a tablet machine.

EXAMPLE 1

An iron vapor phase catalytic reaction tube having a diameter of 2 cm and a height of 50 cm was filled with 80.0 grams of copper chromite catalyst in the form of tablet prepared according to Reference Example and was heated to about 270° C. A mixture of nitrobenzene and methyl alcohol (the mixing ratio by weight being 1 : 4) was dropped into an evaporator at a rate of 30.7 g/hr. The generated vapor was contacted with the catalyst in the reaction tube, while hydrogen gas was passed through the reaction tube at a rate of 96.1./hr. The reaction product was collected for 10 hours after the start of the reaction. After separation, an oil layer was dried over anhydrous sodium sulfate and was subjected to fractional distillation. Thus, a distillate having a boiling point of 190° to 194° C was obtained.

This distillate was cooled to −5° C and the separated crystals were collected by filtration. Thus, 52.0 grams of N,N-dimethylaniline having a melting point of 2.5° C was obtained.

The yield was 86% based on nitrobenzene. The elementary analysis values of the thus obtained compound were as follows:

Elementary analysis (as $C_8H_{11}N$):

|  | C | H | N |
|---|---|---|---|
| Calculated | 79.3% | 9.09% | 11.5% |
| Found | 79.1% | 9.07% | 11.2% |

Further, the filtrate obtained in the crystallization procedure was purified by developing the filtrate by column chromatography using silica gel and n-hexane as a solvent. Thus, 6.0 grams of N-methylaniline was obtained. The elementary analysis values of this compound were as follows:

Elementary analysis (as $C_7H_9N$):

|  | C | H | N |
|---|---|---|---|
| Calculated | 79.5% | 8.4% | 13.1% |
| Found | 79.2% | 8.3% | 13.2% |

EXAMPLE 2

Into an electromagnetically stirring autoclave having a capacity of 500 cc, 10.0 grams of copper chromite catalyst in powder prepared according to Reference Example, 137 grams of 3-methylnitrobenzene and 140 grams of ethyl alcohol were charged and were reacted at 250° C for 20 hours while the pressure was maintained at 50 atmospheres with hydrogen gas.

After the completion of the reaction, the reaction mixture was distilled to obtain 27.5 grams of N-ethyl-3-methylaniline having a boiling point of 119° to 222° C.

The product was further purified by developing it by column chromatography using silica gel and carbon tetrachloride as a solvent. The elementary analysis values of the purified product were as follows:

Elementary analysis (as $C_9H_{13}N$):

|  | C | H | N |
|---|---|---|---|
| Calculated | 80.0% | 9.6% | 10.4% |

| | C | H | N |
|---|---|---|---|
| Found | 79.8% | 9.3% | 10.2% |

EXAMPLE 3

A vapor phase catalytic reaction tube was filled with 80 grams of copper chromite catalyst in the form of tablet prepared according to Reference Example and was heated to about 260° C. A mixture of nitrobenzene and methyl alcohol (the mixing ratio by weight being 1 : 1) was charged in the form of vapor into the catalyst layer at a rate of 24.6 g/hr. in a stream of 90 l./hr. of hydrogen gas.

The reaction product was collected for 5 hours after the start of the reaction and was then treated in the same manner as in Example 1 to obtain 45.5 grams of N-methylaniline.

The boiling point of the purified product was 193° C and its elementary analysis values were as follows:

Elementary analysis (as $C_7H_9N$):

| | C | H | N |
|---|---|---|---|
| Calculated | 79.5% | 8.4% | 13.1% |
| Found | 79.4% | 8.1% | 13.2% |

Further, it was confirmed by gas chromatography analysis that 5.4 grams of N,N-dimethylaniline was formed as a by-product in this example.

EXAMPLE 4

A vapor phase catalytic reaction tube was filled with 72 grams of copper chromite catalyst in the form of tablet prepared according to Reference Example and was heated to about 270° C.

A mixture of nitrobenzene and ethyl alcohol (the mixing ratio by weight being 1 : 5) was charged in the form of vapor into the catalyst layer at a rate of 60.0 g/hr. in a stream of 96 l./hr. of hydrogen gas.

The reaction product was collected for 10 hours after the start of the reaction and was separated into an oil layer and an aqueous layer. The oil layer was dried over anhydrous sodium sulate and ethyl alcohol was then distilled off. To the oil layer was added 21 grams of an 85% aqueous formic acid solution. The mixture was heated under reflux for about one hour and was then distilled. Thus, 109 grams of N,N-diethylaniline having a boiling point of 215° to 216° C was obtained.

The elementary analysis values of the compound purified by developing the compound by column chromatography using silica gel and n-hexane as a solvent were as follows:

Elementary analysis (as $C_{10}H_{15}N$):

| | C | H | N |
|---|---|---|---|
| Calculated | 67.1% | 10.1% | 9.4% |
| Found | 67.4% | 10.4% | 9.6% |

Further, it was confirmed by gas chromatography analysis that 5.0 grams of N-monoethylaniline was also formed as a by-product.

EXAMPLE 5

A vapor phase catalytic reaction tube was filled with 72 grams of copper chromite catalyst in the form of tablet prepared according to Reference Example and was heated to about 260° C. A mixture of nitrobenzene and ethyl alcohol (the mixing ratio by weight being 1 : 1.5) was charged in the form of vapor into the catalyst layer at a rate of 25.0 g/hr. in a stream of 96 l./hr. of hydrogen gas.

The reaction product was collected for 5 hours after the start of the reaction and was then treated in the same manner as in Example 1. Thus, 45.3 grams of N-ethylaniline having a boiling point of 206° to 207° C was obtained.

The elementary analysis values of the purified product were as follows:

Elementary analysis (as $C_8H_{11}N$):

| | C | H | N |
|---|---|---|---|
| Calculated | 79.3% | 9.1% | 11.6% |
| Found | 79.0% | 9.2% | 11.7% |

EXAMPLES 6 to 20

The compounds obtained by reacting an aromatic nitro compound with an aliphatic alcohol in the same manner as in Example 1 are shown in the following table. The present invention should not be construed to be limited to these compounds.

Table

| Example No. | Product | X (nitro) | ROH R | NO₂/ROH Ratio | Amount of catalyst (g) | Rate of $H_2$ gas (l./hr.) | Reaction temperature (°C) | Yield based on nitro compound (%) | Physical constants of product | Elementary analysis values of product (): calculated values |
|---|---|---|---|---|---|---|---|---|---|---|
| 6 | HN—(i)C₃H₇ (phenyl) | H | (i)C₃H₇ | 1/2 | 72 | 96 | 270 | 74.9 | b.p. 212°–213° C /760 mmHg | C 77.4% (77.5%) H 9.20% (9.35%) N 10.00% (10.05%) |
| 7 | H₉C₄(n)—N—(n)C₄H₉ (phenyl) | H | (n)C₄H₉ | 1/7 | 72 | 96 | 310 | 38.4 | b.p. 262°–263° C /760 mmHg | C 82.4% (82.0%) H 11.7% (11.2%) N 6.2% (6.8%) |
| 8 | H₃C—N—CH₃ (3-methylphenyl) | 3-CH₃ | CH₃ | 1/6 | 72 | 96 | 260 | 89.2 | b.p. 115°–119° C /40 mmHg | C 80.5% (80.0%) H 9.47% (9.62%) N 10.61% (10.37%) |
| 9 | HN—(n)C₃H₇ (4-methylphenyl) | 4-CH₃ | (n)C₃H₇ | 1/2 | 72 | 96 | 250 | 92.7 | b.p. 125°–128° C /10 mmHg | C 80.6% (80.5%) H 10.1 (10.06%) N 9.35% (9.39%) |
| 10 | H₅C₂—N—C₂H₅ (4-methylphenyl) | 4-CH₃ | C₂H₅ | 1/5 | 72 | 96 | 280 | 84.5 | b.p. 224°–273° C /760 mmHg | C 81.1% (80.9%) H 10.26% (10.42%) N 8.65% (8.58%) |
| 11 | H—N—CH₃ (2-methylphenyl) | 2-CH₃ | CH₃ | 1/2 | 72 | 96 | 240 | 84.5 | b.p. 94°–97° C /15 mmHg | C 79.7% (79.3%) H 9.07% (9.09%) N 11.40% (11.57%) |
| 12 | H—N—(i)C₄H₉ (phenyl) | H | (i)C₄H₉ | 1/2 | 72 | 96 | 260 | 78.6 | b.p. 110°–113° C /10 mmHg | C 80.8% (80.5%) H 9.98% (10.06%) N 9.26% (9.39%) |
| 13 | H—N—C₂H₅ (2-methylphenyl) | 2-CH₃ | C₂H₅ | 1/2 | 72 | 96 | 250 | 82.1 | b.p. 95°–97° C /10 mmHg | C 79.6% (80.0%) H 9.83% (9.62%) N 10.45% (10.37%) |
| 14 | H—N—(n)C₄H₉ (2-methylphenyl) | 2-CH₃ | (n)C₄H₉ | 1/2 | 72 | 96 | 260 | 71.7 | b.p. 123°–125° C /10 mmHg | C 81.1% (80.9%) H 10.29% (10.42%) N 8.50% (8.58%) |

Table-continued

| Example No. | Product | X | ROH R | NO$_2$/ROH Ratio | Amount of catalyst (g) | Rate of H$_2$ gas (l./hr.) | Reaction temperature (° C) | Yield based on nitro compound (%) | Physical constants of product | Elementary analysis values of product (): calculated values | | |
|---|---|---|---|---|---|---|---|---|---|---|---|---|
| | | | | | | | | | | C | H | N |
| 15 | H—N—CH$_3$ / OCH$_3$ | 3-OCH$_3$ | CH$_3$ | 1/2 | 72 | 96 | 250 | 76.7 | b.p. 126°–129° C /10 mmHg | 70.0 % (70.1 %) | 8.06 % (8.02 %) | 10.19 % (10.21 %) |
| 16 | H$_3$C—N—CH$_3$ / OCH$_3$ | 3-OCH$_3$ | CH$_3$ | 1/7 | 72 | 96 | 280 | 96.8 | b.p. 239°–243° C /760 mmHg | 71.5 % (71.5 %) | 8.60 % (8.61 %) | 9.25 % (9.27 %) |
| 17 | H—N—(n)C$_3$H$_7$ / OCH$_3$ | 3-OCH$_3$ | (n)C$_3$H$_7$ | 1/2 | 72 | 96 | 240 | 73.3 | b.p. 142°–148° C /9 mm Hg | 72.8 % (72.7 %) | 9.07 % (9.09 %) | 8.51 % (8.48 %) |
| 18 | H—N—(n)C$_4$H$_9$ / OCH$_3$ | 2-OCH$_3$ | (n)C$_4$H$_9$ | 1/2 | 72 | 96 | 270 | 64.9 | b.p. 145°–148° C /16 mmHg | 73.5 % (73.4 %) | 9.20 % (9.14 %) | 7.87 % (7.82 %) |
| 19 | H—N—C$_2$H$_5$ / OCH$_3$ | 4-OCH$_3$ | C$_2$H$_5$ | 1/2 | 72 | 96 | 250 | 87.0 | b.p. 138°–144° C /24 mmHg | 71.4 % (71.5 %) | 8.59 % (8.61 %) | 9.33 % (9.27 %) |
| 20 | H—N—(n)C$_4$H$_9$ / OCH$_3$ | 4-OCH$_3$ | (n)C$_4$H$_9$ | 1/2 | 72 | 96 | 280 | 84.1 | b.p. 150°–156° C /11 mmHg | 73.8 % (73.3 %) | 9.10 % (9.14 %) | 7.85 % (7.82 %) |

What is claimed is:

1. A process for producing aromatic secondary or tertiary amino compounds with the formula,

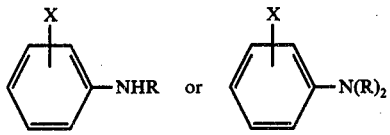

wherein X is a hydrogen atom, a methyl group or a methoxy group, and R is methyl, ethyl, n-propyl isopropyl, n-butyl, isobutyl or sec.-butyl, which comprises reacting hydrogen, an aromatic nitro compound of the formula,

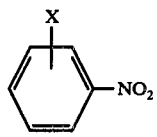

wherein X is as defined above, and an alcohol of the formula,

ROH wherein R is as defined above, in the presence of a catalyst of copper chromite consisting essentially of copper chromite of the formula $CuOCuCr_2O_4$, or a catalyst of copper chromite consisting essentially of as a main ingredient copper chromite of the formula $CuOCuCr_2O_4$ and as a promoter at least one member selected from the group consisting of Fe, Ni, Ba, Mg and Mn.

2. A process according to claim 1, wherein said reaction is carried out under a vapor phase condition.

3. A process according to claim 1, wherein 1 to 20 moles of the alcohol per mole of the aromatic nitro compound is used.

4. A process according to claim 1, wherein said reaction is carried out at a temperature of 150° to 400° C.

5. A process according to claim 1, wherein said reaction is carried out while a pressure of 20 to 100 atmospheres is maintained with hydrogen gas.

* * * * *